United States Patent [19]

Yabushita et al.

[11] Patent Number: 4,696,916
[45] Date of Patent: Sep. 29, 1987

[54] INTRAVENOUS NUTRIENT

[75] Inventors: Yasunori Yabushita, Nara; Kunihiko Takagi, Kyoto, both of Japan

[73] Assignee: Unitika Ltd., Hyogo, Japan

[21] Appl. No.: 404,743

[22] Filed: Aug. 3, 1982

[51] Int. Cl.$^4$ ............................................. A61K 31/70
[52] U.S. Cl. ...................................... 514/25; 514/23; 514/53; 514/54; 514/61
[58] Field of Search ......................... 424/180; 536/119; 514/23, 25, 53, 54, 61

[56] References Cited

U.S. PATENT DOCUMENTS 3,600,186  8/1971  Mattson et al. .................. 536/119
3,714,144  1/1973  Feuge et al. ..................... 536/119

Primary Examiner—Johnnie R. Brown
Assistant Examiner—Elli Peselev
Attorney, Agent, or Firm—Sughrue, Mion, Zinn, Macpeak & Seas

[57] ABSTRACT

The present invention is an intravenous nutrient which contains a fatty acid ester of carbohydrate and water. The nutrient fluid contains a carbohydrate component and a fat component, has an excellent stability in solution, and is used in nutrient fluid therapy for individuals who cannot take food orally. The nutrient fluid is especially suitable as a high calorie intravenous nutrient.

21 Claims, No Drawings 4,696,916

INTRAVENOUS NUTRIENT

FIELD OF THE INVENTION

The present invention relates to an intravenous nutrient and, more specifically, to an intravenous nutrient containing a fatty acid ester of carbohydrate.

BACKGROUND OF THE INVENTION

People normally extract necessary nutrients from the food they eat. However, for various reasons, a person may be unable to eat food. In that past, in order to supply nutrients to such people, nutrient fluid therapy has been used. Nutrient fluid therapy is a method in which an intravenous nutrient, for example, a glucose solution is injected into a peripheral vein by drip infusion. The glucose solution used usually has a concentration of about 5 weight %. Furthermore, the volume of the nutrient fluid which can be supplied to a human body is about 2 to 3 liters per day. Accordingly, only about 400–600 calories can be supplied per day by this method at best. An increase inthe glucose concentration raises osmotic pressure and, as a result, walls or peripheral blood vessels are irritated which predisposes a person to phlebitis; therefore, it has been difficult to supply more than 400 to 600 calories per day by this method.

Presently, two types of high calorie nutrient fluid therapies are being developed which make possible the administration of nutrients having a calorific value as high as 2,000 to 3,000 calories.

In accordance with one method, called one Dubrick method as described in Dudrick, S. J., Surg. Forum, 18, 356 (1967), a nutrient fluid containing glucose having a concentration as high as 20–35 weight % besides amino acids and electrolytes is infused into a central vein having great blood flow through a catheter. By this method, nutrients having a calorific value as high as about 3,000 calories can be given. The intravenous nutrient used in this method is homogeneous and is therefore desirable because it can be handled easily. This method, however, poses the following problems: A catheter must remain placed in a central vein which creates a risk of complications; there is a problem of nutritional balance in that essential fatty acids must be given separately; in addition, special care must be exercised when the method is applied to diabetics since a nutrient fluid containing a high concentration of glucose is employed.

In accordance with the other method, called the Wretlind method as described in Wretlind, A., Nutr. Metab., 14, 1 (1972), an intravenous nutrient containing amino acids, electrolytes, and glucose is given on one hand and, separately, one containing a fat emulsion is simultaneously given. In accordance with this method, the fat is said to account for more than about 50% of the total calories. This method has an advantage in that an intravenous nutrient can be infused through peripheral veins and, moreover, the nutritional balance is good because fats can be given in addition to carbohydrate. Since fats are immiscible with water, they are used, as stated earlier, as a fat emulsion prepared by emulsifying fats by the addition of an emulsifying agent such as yolk lecithin. However, an intravenous nutrient containing such emulsified fats raises a problem that fat particles may gradually aggegate and create a blockage making the infusion through peripheral veins difficult. This method also poses a problem that the infusion from two sites is necessary.

Besides the foregoing methods, there has been proposed a method (One Pack method as described in Hikasa. Y., Japanese J. of Parenteral & Entral Nutrition, 2, 559 (1980)) in which a mixture of amino acids, electrolytes, glucose, and a fat emulsion is infused. However, this method is not desirable because every component must be mixed immediately before use because the stability of the nutrient fluid is unsatisfactory.

A known fatty acid ester of carbohydrate is described in L. Osipow, F. D. Snell, Ind. Eng. Chem., 48, 1459 (1956), T. Ishizuka, YUKAGAKU, 21, 408 (1972), and U.S. Pat. No. 2,931,802. A fatty acid ester of carbohydrate is known to be soluble in water and have surface activity. Such as ester is known to be useful as an innocuous food additive, emulsifying agent or detergent. A fatty acid ester of carbohydrate can be prepared, for example, as described in the foregoing L. Osipow, F. D. Snell, Ind. Eng. Chem., 48, 1459 (1956), by an interesterification reaction between a carbohydrate and an alkyl ester of a fatty acid. It is also well known that a fatty acid ester of carbohydrate can be obtained by a reaction between a carbohydrate and a fatty acid halide, for example, as described in the foregoing T. Ishizuka, YUKAGAKU, 21, 408 (1972).

SUMMARY OF THE INVENTION

A primary object of the present invention is to provide a high calorie intravenous nutrient. Another object is to provide an intravenous nutrient capable of being infused through peripheral veins. Yet another object is to provide an intravenous nutrient containing a fat component. Still another object is to provide an intravenous nutrient which is so stable that particles will not aggregate, thicken or create blockage. Another object is to provide an intravenous nutrient which will not give rise to aggregation upon the addition of a carbohydrate or a fat or even upon the further simultaneous addition of other nutrients. Yet another object is to provide an intravenous nutrient which creates low osmotic pressure relative to the calories it can supply.

The present inventors have assiduously made many investigations in order to attain these ends. As a result, they have found that the use of a fatty acid ester of carbohydrate is effective in attaining these ends and, based on this finding, have completed the present invention.

Thus the present invention is an intravenous nutrient comprising a fatty acid ester of carbohydrate and water.

DETAILED DESCRIPTION OF THE INVENTION

The present invention is a fatty acid ester of carbohydrate contained in the intravenous nutrient. Once the ester is present in the human body, it is hydrolyzed to a sugar and a fatty acid by the action of enzymes and so forth. Therefore, the use of the intravenous nutrient of the present invention enables a human subject to ingest calories from both the carbohydrate and the fatty acid. Accordingly, the nutrient fluid is useful as a source of calories and, even when it contains a fatty acid ester of carbohydrate in such a concentration that it will not cause phlebitis on its introduction through peripheral veins, can supply a person with nutrients having a calorific value as high as about 2,000 to 3,000 per day. The intravenous nutrient of the present invention is also excellent with respect to nutritional balance and is useful in the supply of essential fatty acids that are indispensable for long-term fluid therapy. The nutrient fluid is also in that it results in the creation of low osmotic pressure relative to the calorific value contained therein.

The fatty acid ester of carbohydrate used in the present invention itself dissolves in water because of its additional activity as a surface active agent. Accordingly, the ester creates no concern over problems such as insolubility in water. Moreover, the fatty acid ester of carbohydrate is very advantageous in that a fat can also be incorporated therein in addition to amino acids, carbohydrates, and electrolytes. It is also advantageous that the kind of carbohydrates and fatty acids can be freely chosen and some of the fatty acids such as mycomycin, are expected to have antibacterial activity.

The term "fatty acid ester of carbohydrate" as used in the present invention means a compound resulting from an ester combination of a carbohydrate with at least one fatty acid. In the present invention, presently known fatty acid esters of carbohydrate of different kinds can be suitably employed. However, the ester are used after isolation and purification by means of, for example, chromatography and so on. It is also possible to use as a fatty acid ester of carbohydrate those wherein the number of fatty acids to be combined with the sugar is optionally varied according to the number of esterifiable hydroxyl groups of the carbohydrate. In addition, esters may be used wherein several different kinds of fatty acids are combined with a single carbohydrate.

Carbohydrate which are useful in connection with this invention include monosaccharides such as, for example, glycerose, dihydroxyacetone, erythrose, threose, arabinose, ribose, lyxose, xylose, ribulose, xylulose, glucose, mannose, allose, altrose, talose, galactose, idose, gulose, fructose, psicose, tagatose, sorbose, aldoheptose, ketoheptose, ketooctose, ketononose, deoxypentose, deoxyhexose, dideoxyhexose, alditol, xylitol, sorbitol, arabitol, mannitol, galactitol, heptitol, uronic acid, ketoaldonic acid, ascorbic acid, amino sugars, and sialic acid; oligosaccharides such as xylooligosaccharide, galactooligosaccharide, glucooligosaccharide, e.g., maltose, mannooligosaccharide, fructooligosaccharide, glucosaminooligosaccharide, uronic acid-oligosaccharide, and heterooligosaccharide, e.g., sucrose and lactose; homopolysaccharides such as pentosan and hexosan; heteropolysaccharides such as mucopolysaccharides and glucosaminoglucin; especially, monosaccharides and oligosaccharides are preferable. The preferred examples of the monosaccharides include glucose, fructose, xylitol and sorbitol, and the preferred examples of the oligosaccharides include an oligosaccharides such as maltose, sucrose and lactose comprising 2 to 6 sugar unit residues as a structural monomer and having at least one glucopyranose residue.

Fatty acids which are useful in connection with the present invention include saturated fatty acids such as, for example, formic acid, acetic acid, propionic acid, butyric acid, valeric acid, caproic acid, enanthic acid, caprylic acid, pelargonic acid, capric acid, lauric acid, myristic acid, palmitic acid, stearic acid, arachidic acid, behenic acid, lignoceric acid, and cerotic acid; unsaturated fatty acids such as obtusilic acid, linderic acid, tsuznic acid, physeteric acid, myristoleic acid, palmitoleic acid, petroselinic acid, oleic acid, ricinoleic acid, vaccenic acid, linoleic acid, linolenic acid, linoelaidic acid, elaidic acid, eleostearic acid, punicic acid, parinaric acid, gadoleic acid, arachidonic acid, eicosadienoic acid, eicosatrienoic acid, eicosenoic acid, erucic acid, and mycomycin; and branched-chain fatty acids such as phthienoic acid, mycocerosic acid, mycolic acid, iso-acid, tuberculostearic acid, and sterculic acid; especially, unsaturated fatty acids are preferable. As fatty acids, long-chain fatty acids, especially long-chain unsaturated fatty acids, are preferable. As long-chain unsaturated fatty acids, the oleic acid, linoleic acid and linolenic acid are more preferred.

Especially preferable fatty acid esters of carbohydrate employed in the present invention include esters which are formed by a reaction between monosaccharides such as glucose, fructose, xylitol, and sorbitol or oligosaccharides such as maltose, sucrose and lactose comprising 2 to 6 sugar unit residues as a structural monomer and having at least one glucopyranose residue; and long-chain unsaturated fatty acids such as oleic acid, linoleic acid, linolenic acid and so forth.

The intravenous nutrient of the present invention can be prepared by dissolving a fatty acid ester of carbohydrate in water. The concentration of a fatty acid ester of carbohydrate in the intravenous nutrient is preferably about 0.001 to 80 wt %, more preferably 0.1 to 60 wt %. Most preferable the concentration is about .5 to 30 wt % when the infusion is performed through peripheral veins. The concentration of the fatty acid ester of carbohydrate is preferably 5 wt % or more when it is included as a source of calories. However, it may be present in an amount of 0.001 wt %, preferably 0.1 wt % or more when it is used to provide surface activity to emulsify and disperse other additives such as nutrients.

The intravenous nutrient of the present invention can contain, if necessary, carbohydrates, electrolytes such as sodium and potassium, amino acids such as leucine, arginine, lysin, and alanin, fats, trace of elements such as copper and iron, and vitamins. Moreover, the nutrient fluid can contain medicines such as, for example, antibiotics and anticancer agents.

The present invention will now be illustrated in greater detail by reference to the following examples and comparative examples which are given here for illustrative purposes only and are by no means intended to limit the scope of the invention.

EXAMPLE 1

Interesterification was carried out by heating glucose andmethyl linoleate at 100° C. for 3 hours under atmospheric pressure of N2 gas in the presence of potassium carbonate as a catalyst to synthesize glucose linoleate. Glucose monolinoleate was then isolated and purified by means of chromatography.

In 100 ml of physiological saline solution for injection was dissolved 20 g of glucose monolinoleate obtained above to afford a homogeneous solution. The solution was administered to a rabbit weighing 2.5 kg through an aural vein at the rate of 1 ml/min. The administration was continued for 20 days in a dose of 100 ml/day, whereby any decrease in the body weight of the rabbit was not observed.

COMPARATIVE EXAMPLE 1

A solution of 20 g of glucose in 100 ml of physiological saline solution for injection was administered in the same manner as described hereinabove to a rabbit weighing 2.4 kg in a dose of 100 ml/day for 20 days, whereby the body weight decreased to 1.5.

From the foregoing results in Example 1 and Comp. Example 1, it was observed that linoleic acid glucose monoester is useful as a calorie source.

EXAMPLE 2

Interesterification was carried out by heating fructose and ethyl oleate at 100° C. for 3 hours under atmospheric pressure of $N_2$ gas in the presence of potassium carbonate as a catalyst to synthesize fructose oleates. The fructose dioleate was then isolated and purified by means of chromatography.

The fructose dioleate obtained above was administered to a rabbit in the same manner as in Example 1 in a dose of 85 ml/day for 20 days, whereby any decrease in the body weight of the rabbit was not observed.

EXAMPLE 3

Interesterification was carried out by heating sorbitol and methyl oleate at 85° C. for 3 hours under atmospheric pressure of $N_2$ gas in the presence of potassium carbonate as a catalyst to synthesize sorbitol oleates. The sorbitol monooleate was then isolated and purified by means of chromatography.

The oleic acid sorbitol monoester obtained above was administered to a rabbit in the same manner as in Example 1 in a dose of 100 ml/day for 20 days, whereby any decrease in the body weight of the rabbit was not observed.

EXAMPLE 4

Ten grams of the glucose monolinoleate isolated and purified in Example 1 was mixed with a solution consisting of 30 ml of a 50 wt % glucose solution, 75 ml of a commercial 5 wt % amino acid fluid for transfusion (5% Ispol, prepared by Daigoeiyo Chemical Co., Ltd.), 20 ml of a commercial electrolyte fluid for transfusion (Solita-T3, prepared by Shimizu Pharmaceutical Co., Ltd.), and 25 ml of distilled water for injection to afford a homogeneous solution.

The solution obtained above was administered through an aural vein to a rabbit weighing 2.6 kg at the rate of 1 ml/min. After the administration, the blood pressure, the respiration rate, and the heart beat rate of the rabbit were measured and any change was not observed in all three. The administration of the same solution to a rabbit in a dose of 100 ml/day for one month increased the body weight of the rabbit by 0.2 kg.

COMPARITIVE EXAMPLE 2

A solution as in Example 4, but devoid of added glucose monolinoleate was administered to a rabbit according to the same method as in Example 4 in does of 100 ml/day for a month, the body weight of the rabbit decreased by 0.6 kg.

EXAMPLE 5

The addition of a fat emulsion (a mixture of 10 g of soybean oil, 1.2 g of egg yolk phosphatides, and 25 g of glycerol) to the solution obtained in Example 4 afforded a clear, homogeneous solution.

COMPARATIVE EXAMPLE 3

The addition of the same fat emulsion of Example 5 to a solution as in Example 4, but devoid of added glucose monolinoleate made the solution cloudy and white.

EXAMPLE 6

When 10 g of soybean oil and 5 g of the glucose monolinoleate isolated and purified in Example 1 were mixed with 100 ml of distilled water for injection and the resulting mixture was subjected to an ultrasonic treatment for 2 hours using a water bath-type sonicator, a clear, homogeneous solution was obtained.

From the foregoing results, it was observed that linoleic acid glucose monoester is useful as an emulsifying agent for a fat in a nutrient fluid for transfusion.

While the invention has been described in detail and with reference to specific embodiments thereof, it will be apparent to one skilled in the art that various changes and modifications can be made therein without departing from the spirit and scope thereof.

What is claimed is:

1. An intravenous nutrient composition containing a fatty acid ester of carbohydrate selected from the group consisting of a monosaccharide, an oligosaccharide, a homopolysacharide, and a heteropolysaccharide, and water, wherein the amount of the fatty acid ester of carbohydrate is from about 0.001 to about 80% by weight based on the total amount of the fatty acid ester of carbohydrate and water, the fatty acid ester of carbohydrate is dissolved in the water and the fatty acid is at least one fatty acid selected from the group consisting of a saturated fatty acid, an unsaturated fatty acid and a branched-chain fatty acid, said composition being administerable by intravenous injection.

2. The intravenous nutrient according to claim 1, wherein the fatty acid ester of carbohydrate is a long-chain fatty acid ester of carbohydrate.

3. The intravenous nutrient according to claim 1, wherein the fatty acid ester of carbohydrate is a long-chain fatty acid ester of monosaccharide.

4. The intravenous nutrient according to claim 1, wherein the fatty acid ester of carbohydrate is a long-chain fatty acid ester of oligosaccharide.

5. The intravenous nutrient according to claim 1, wherein the fatty acid ester of carbohydrate contains a plurality of long-chain fatty acids.

6. The intravenous nutrient according to claim 1, wherein the fatty acid ester of carbohydrate contains a plurality of fatty acids and the carbohydrate is a monosaccharide.

7. The intravenous nutrient according to claim 1, wherein the fatty acid ester of carbohydrate contains a plurality of long-chain fatty acids and the carbohydrate is a monosaccharide.

8. The intravenous nutrient according to claim 1, wherein the fatty acid ester of carbohydrate contains a plurality of fatty acids and the carbohydrate is an oligosaccharide.

9. The intravenous nutrient according to claim 1, wherein the fatty acid ester of carbohydrate contains a plurality of long-chain fatty acids and the carbohydrate is an oligosaccharide.

10. The intravenous nutrient as claimed in any of claims 2, 3, 4, 5, 7 or 9, wherein the long-chain fatty acid is a long-chain unsaturated fatty acid.

11. The intravenous nutrient as claimed in any of claims 3, 6 or 7, wherein the monosaccharide is a member selected from the group consisting of glucose, fructose, xylitol, and sorbitol.

12. The intravenous nutrient as claimed in any of claims 4, 8 or 9, wherein the oligosaccharide is a substance comprising 2 to 6 sugar unit residues as a structural monomer and having at least one glucopyranose residue.

13. The intravenous nutrient as claimed in any of claims 4, 8 or 9, wherein the oligosaccharide is a member selected from the group consisting of maltose, sucrose and lactose.

14. The intravenous nutrient as claimed in any of claims 2, 3, 4, 5, 7 or 9, wherein the long-chain fatty acid is a member selected from the group consisting of oleic acid, linoleic acid, and linolenic acid.

15. The intravenous nutrient according to claim 1, which contains the fatty acid ester of carbohydrate in an amount of from 0.1 to 60 wt % relative to the total amount of the fatty acid ester of carbohydrate and water.

16. The intravenous nutrient of claim 5 wherein the number of fatty acids is varied up to the number of esterifiable hydroxyl groups of the carbohydrate.

17. The intravenous nutrient of claim 6 wherein the number of fatty acids is varied up to the number of esterifiable hydroxyl groups of the carbohydrate.

18. The intravenous nutrient of claim 7 wherein the number of fatty acids is varied up to the number of esterifiable hydroxyl groups of the carbohydrate.

19. The intravenous nutrient of claim 8 wherein the number of fatty acids is varied up to the number of esterifiable hydroxyl groups of the carbohydrate.

20. The intravenous nutrient of claim 9 wherein the number of fatty acids is varied up to the number of esterifiable hydroxyl groups of the carbohydrate.

21. A process for providing a high calorie nutrient to a patient which comprises intravenously administering to said patient an intravenous nutrient composition containing a fatty acid ester of carbohydrate selected from the group consisting of a monosaccharide, an oligosaccharide, a homopolysaccharide, and a heteropolysaccharide, and water, wherein the amount of the fatty acid ester of carbohydrate is from about 0.001 to about 80% by weight based on the total amount of the fatty acid ester of carbohydrate and water, the fatty acid ester of carbohydrate is dissolved in the water and the fatty acid is at least one fatty acid selected from the group consisting of a saturated fatty acid, an unsaturated fatty acid and a branched-chain fatty acid, said composition being administerable by intravenous injection.

* * * * *